US012078696B2

United States Patent
Zhao et al.

(10) Patent No.: US 12,078,696 B2
(45) Date of Patent: Sep. 3, 2024

(54) SILENT CALIBRATION FOR MAGNETIC RESONANCE IMAGING

(71) Applicant: GE Precision Healthcare LLC, Wauwatosa, WI (US)

(72) Inventors: Xiaoli Zhao, New Berlin, WI (US); Kang Wang, Sussex, WI (US); Hua Li, Sussex, WI (US); Zhenghui Zhang, Buffalo Grove, IL (US); Florian Wiesinger, Freising (DE); Ty A. Cashen, Madison, WI (US); Rolf Schulte, Freising (DE)

(73) Assignee: GE Precision Healthcare LLC, Wauwatosa, WI (US)

( * ) Notice: Subject to any disclaimer, the term of this patent is extended or adjusted under 35 U.S.C. 154(b) by 91 days.

(21) Appl. No.: 17/938,465

(22) Filed: Oct. 6, 2022

(65) Prior Publication Data

US 2024/0118356 A1    Apr. 11, 2024

(51) Int. Cl.
*G01V 3/00* (2006.01)
*A61B 5/055* (2006.01)
*G01R 33/20* (2006.01)
*G01R 33/561* (2006.01)

(52) U.S. Cl.
CPC .............. *G01R 33/20* (2013.01); *A61B 5/055* (2013.01); *G01R 33/5611* (2013.01)

(58) Field of Classification Search
CPC ...... G01R 33/20; G01R 33/5611; A61B 5/055
USPC ........................................................ 324/307
See application file for complete search history.

(56) References Cited

U.S. PATENT DOCUMENTS

| 6,879,156 B1 | 4/2005 | Chesler |
| 8,278,924 B2 | 10/2012 | Fuderer |
| 10,088,539 B2 | 10/2018 | Wiesinger |
| 10,359,487 B2 | 7/2019 | Smink |

(Continued)

FOREIGN PATENT DOCUMENTS

| CN | 103876739 A | * | 6/2014 | ......... G01R 33/5611 |
| JP | 2010012270 A | * | 1/2010 | ......... G01R 33/3415 |
| RU | 2660401 C1 | * | 7/2018 | ........... G01R 33/385 |

OTHER PUBLICATIONS

Alibek et al., "Acoustic noise reduction in MRI using Silent Scan: an initial experience", Diagn Interv Radiol. Jul.-Aug. 2014;20(4):360-3, 4 pages.

(Continued)

*Primary Examiner* — Walter L Lindsay, Jr.
*Assistant Examiner* — Frederick Wenderoth

(57) ABSTRACT

A method for generating an image of an object with a magnetic resonance imaging (MM) system is presented. The method includes first performing a calibration scan of the object. The calibration scan is performed with a zero echo time (ZTE) radial sampling scheme to obtain calibration k-spaces for surface coil elements and a body coil of the MRI system. The calibration scan is performed in such a manner that the endpoints of calibration k-space lines in each calibration k-space follow a spiral path. A plurality of calibration parameters are then obtained from the plurality of calibration k-spaces. A second scan of the object is then performed to acquire the MR image data. The image of the object is then generated based on the plurality of calibration parameters and the MR image data.

19 Claims, 6 Drawing Sheets

(56) References Cited

U.S. PATENT DOCUMENTS

| | | |
|---|---|---|
| 11,360,172 B2 | 6/2022 | Eggers |
| 2013/0113486 A1* | 5/2013 | Imamura .............. G01R 33/341 324/322 |
| 2022/0057463 A1 | 2/2022 | He |

OTHER PUBLICATIONS

Madio et al., "Ultra-fast imaging using low flip angles and FIDs", Magn Reson Med. Oct. 1995;34(4):525-9, 5 pages.

* cited by examiner

SILENT CALIBRATION FOR MAGNETIC RESONANCE IMAGING

BACKGROUND

Embodiments disclosed in the present invention relate to medical imaging technologies, and more specifically to a method for obtaining magnetic resonance imaging (MRI) data and a magnetic resonance imaging system.

As a medical imaging modality, Magnetic resonance imaging (MRI), can obtain images of the human body without using X-rays or other ionizing radiation. MRI uses a magnet having a strong magnetic field to generate a static magnetic field B0. When a part of the human body to be imaged is positioned in the static magnetic field B0, nuclear spin associated with hydrogen nuclei in human tissue is polarized, so that the tissue of the to-be-imaged part generates a longitudinal magnetization vector at a macroscopic level. After a radio-frequency field B1 intersecting the direction of the static magnetic field B0 is applied, the direction of rotation of protons changes so that the tissue of the to-be-imaged part generates a transverse magnetization vector at a macroscopic level. After the radio-frequency field B1 is removed, the transverse magnetization vector decays in a spiral manner until it is restored to zero. A free induction decay signal is generated during decay. The free induction decay signal can be acquired as a magnetic resonance signal, and a tissue image of the to-be-imaged part can be reconstructed based on the acquired signal.

A calibration scan is very important for the MRI system as it is used for auto coil selection, channel compression, parallel imaging and image intensity correction. The calibration scan acquires low resolution surface coil and body coil images. Cartesian three-dimensional (3D) gradient technique is commonly used for calibration scan in the MRI system. Although Cartesian 3D calibration is very fast, it may cause significant signal dephasing in the calibration data at certain areas. In addition, it is very loud due to powerful gradients. In order to reduce the noise level, the gradient slew rate has to be significantly derated, which exacerbates the signal dephasing. The signal dephasing in calibration data may in turn introduce various quality issues to application images, such as shading, local signal loss, signal void in vessel, etc.

Therefore, there is a need for an improved calibration technique for the magnetic resonance imaging system and method.

BRIEF DESCRIPTION

In accordance with an embodiment of the present technique, a method for generating an image of an object with a magnetic resonance imaging (MRI) system is provided. The method includes performing a calibration scan of the object with a spiral zero echo time (ZTE) radial sampling scheme to obtain a plurality of calibration k-spaces. The endpoints of calibration k-space lines in each calibration k-space follow a spiral path. The method further includes obtaining a plurality of calibration parameters from the plurality of calibration k-spaces and performing a second scan of the object to acquire MR image data. Finally, the method includes generating the image of the objected based on the plurality of calibration parameters and the MR image data In accordance with another embodiment of the present technique, a magnetic (MRI) system is provided. The MRI system includes a magnet configured to generate a polarizing magnetic field about at least a portion of an object arranged in the MRI system. The MRI system also includes a gradient coil assembly including a readout gradient coil, a phase gradient coil, a slice selection gradient coil configured to apply at least one gradient field to the polarizing magnetic field. The MRI system further includes a radio frequency (RF) system configured to apply an RF field to the object and to receive magnetic resonance signals from the object and a processing system. The processing system is configured to perform a calibration scan of the object with a spiral zero echo time (ZTE) radial sampling scheme to obtain a plurality of calibration k-spaces where endpoints of calibration k-space lines in each calibration k-space follow a spiral path. The processing system is further configured to obtain a plurality of calibration parameters from the plurality of calibration k-spaces. A second scan of the object is further performed to acquire the MR image data and the image of the object is then generated based on the plurality of calibration parameters and the MR image data.

DRAWINGS

These and other features, aspects, and advantages of the present invention will become better understood when the following detailed description is read with reference to the accompanying drawings in which like characters represent like parts throughout the drawings, wherein.

Figure 5:
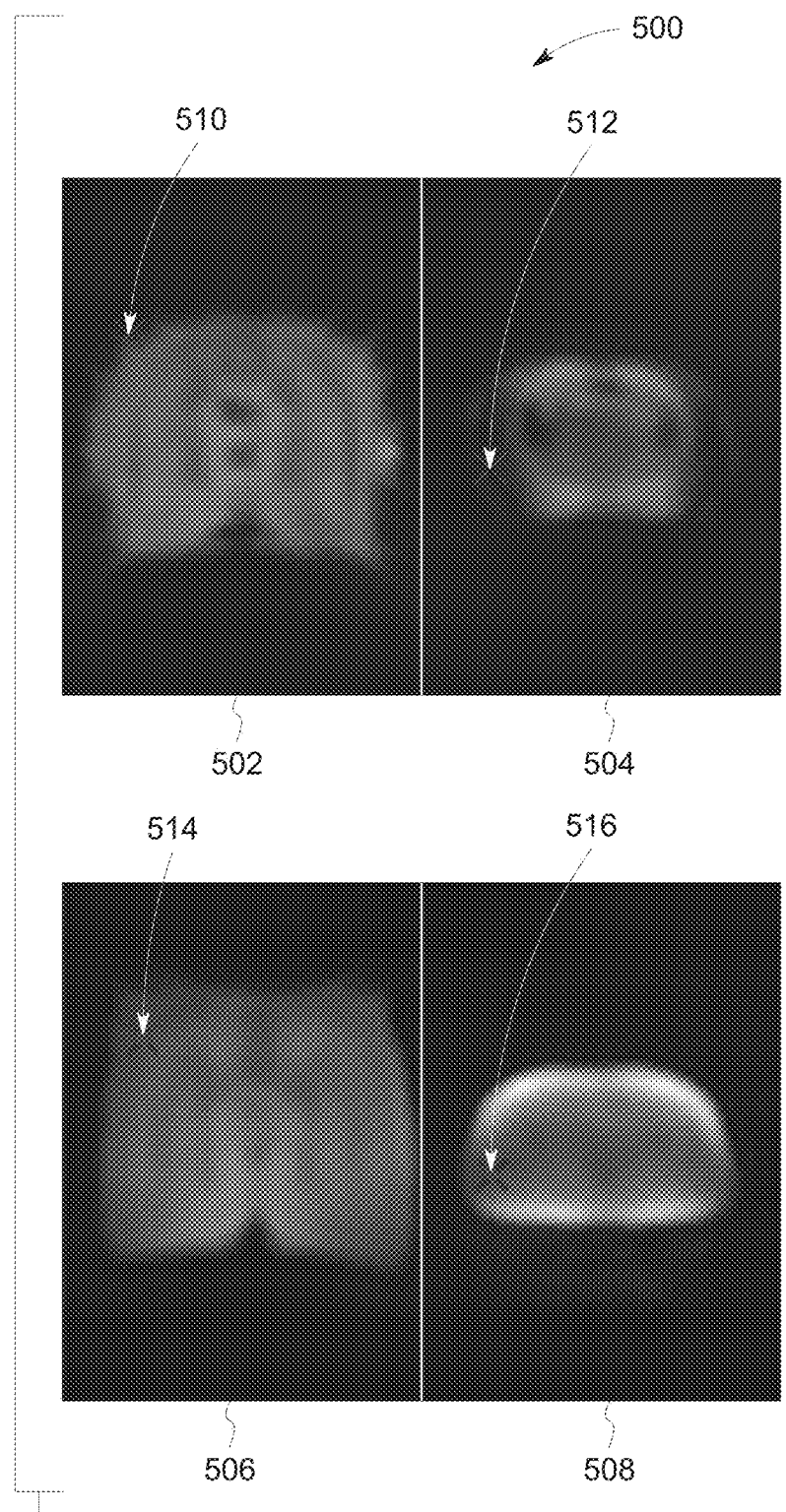
Figure 6:
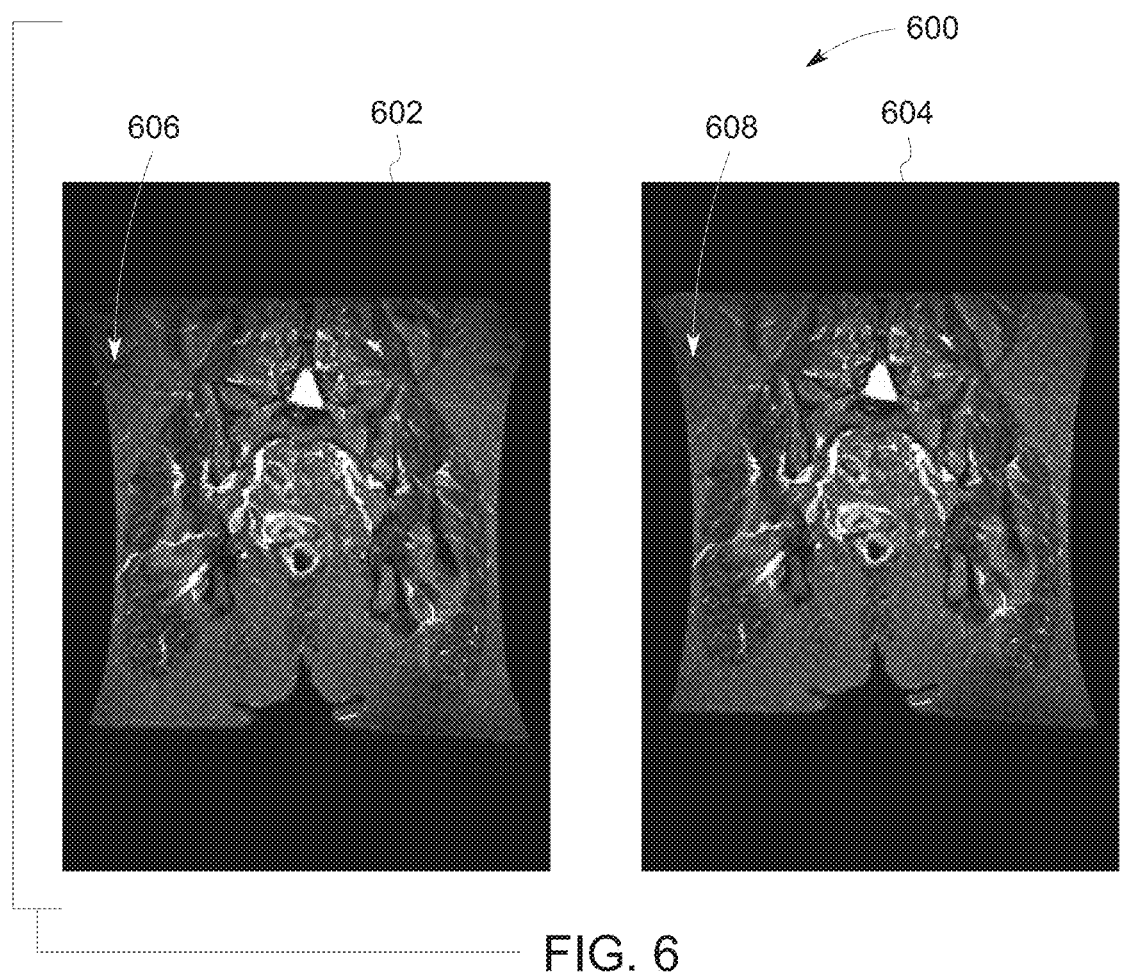

FIG. 5 is another schematic diagram depicting a comparison of images obtained with the cartesian 3D calibration technique and the spiral ZTE radial calibration technique, in accordance with an embodiment of the present technique; and FIG. 6 is yet another schematic diagram depicting a comparison of images obtained with the cartesian 3D calibration technique and the spiral ZTE radial calibration technique, in accordance with an embodiment of the present technique.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments. Furthermore, the terms "circuit" and "circuitry" and "controller" may include either a single component or a plurality of components, which are either active and/or passive and are connected or otherwise coupled together to provide the described function.

In magnetic resonance imaging (MM), an object is placed in a magnet. When the object is in the magnetic field generated by the magnet, magnetic moments of nuclei, such as protons, attempt to align with the magnetic field but process about the magnetic field in a random order at the nuclei's Larmor frequency. The magnetic field of the magnet is referred to as B0 and extends in the longitudinal or z direction. In acquiring a MR image, a magnetic field (referred to as an excitation field B1), which is in the x-y plane and near the Larmor frequency, is generated by a radio-frequency (RF) coil and may be used to rotate, or "flip," the net magnetic moment (or net magnetization) $M_z$ of the nuclei from the z direction to the transverse or x-y plane. This flip of the net magnetic moment $M_z$ of the nuclei is measured by a flip angle which is the amount of rotation the net magnetization experiences during the application of the RF pulse to the RF coil. A signal, which is referred to as a MR signal, is emitted by the nuclei, after the excitation signal B1 is terminated. To use the MR signals to generate an image of an object, magnetic field gradient pulses ($G_x$, $G_y$, and $G_z$) are used. The gradient pulses are used to scan through the k space, the space of spatial frequencies or inverse of distances. A Fourier relationship exists between the acquired MR signals and an image of the object, and therefore the image of the object can be derived by reconstructing the MR signals. The images of the object may include two dimensional (2D) or three-dimensional (3D) images.

Figure 1:
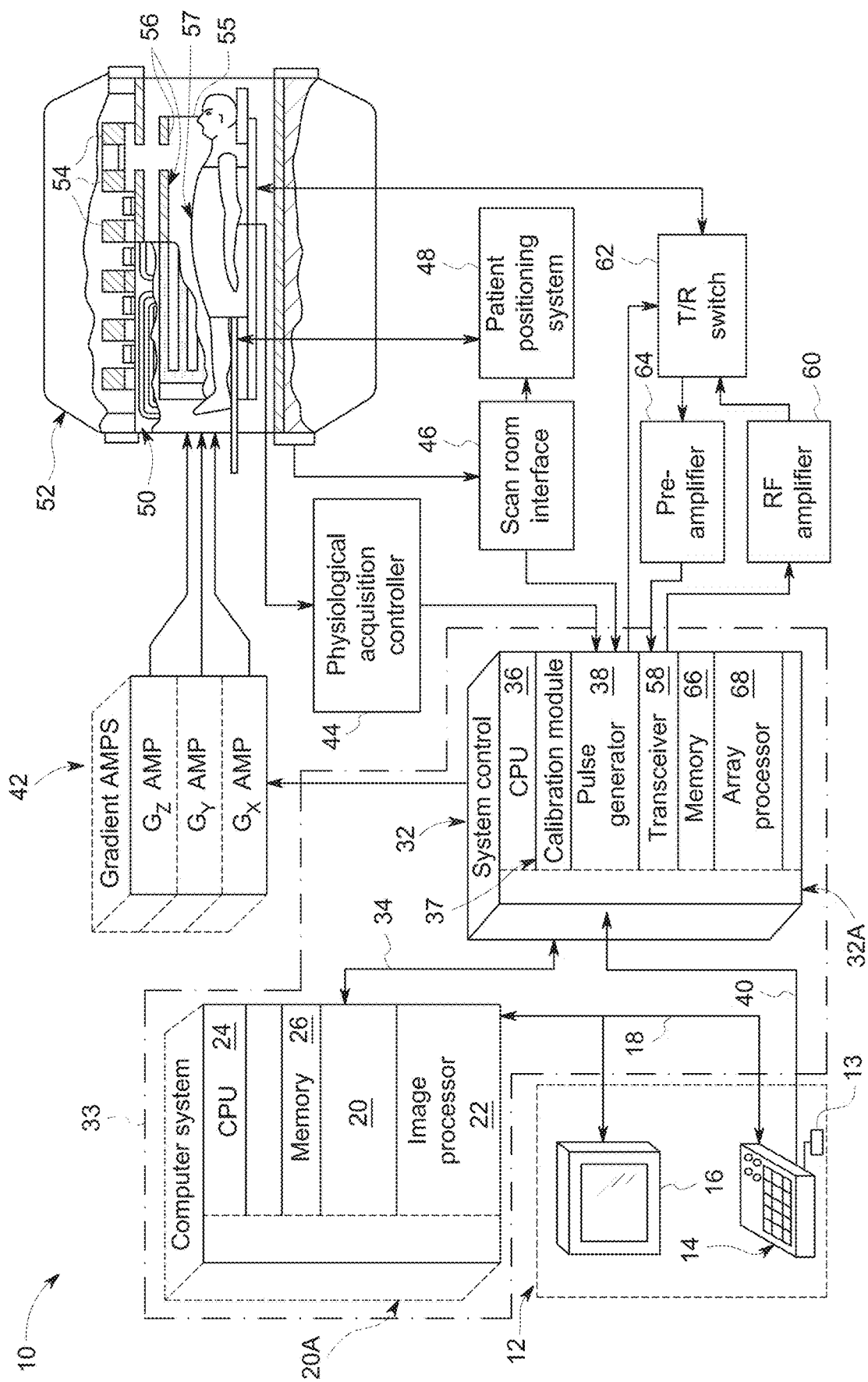
FIG. 1 is a schematic diagram of an exemplary magnetic resonance imaging (MRI) system, in accordance with an embodiment of the present technique.

Embodiments of the present disclosure will now be described, by way of an example, with reference to the figures, in which FIG. 1 is a schematic diagram of a magnetic resonance imaging (MM) system 10. Operation of the system 10 may be controlled from an operator console 12, which includes an input device 13, a control panel 14, and a display screen 16. The input device 13 may be a mouse, joystick, keyboard, track ball, touch activated screen, light wand, voice control, and/or other input device. The input device 13 may be used for interactive geometry prescription. The console 12 communicates through a link 18 with a computer system 20 that enables an operator to control the production and display of images on the display screen 16. The link 18 may be a wireless or wired connection. The computer system 20 may include modules that communicate with each other through a backplane 20a. The modules of the computer system 20 may include an image processor module 22, a central processing unit (CPU) module 24, and a memory module 26 that may include a frame buffer for storing image data arrays, for example. The computer system 20 may be linked to archival media devices, permanent or back-up memory storage or a network for storage of image data and programs and communicates with Mill system control 32 through a high-speed signal link 34. The Mill system control 32 may be separate from or integral with the computer system 20. The computer system 20 and the MRI system control 32 collectively form an "MRI controller" 33 or "controller".

In the exemplary embodiment, the MRI system control 32 includes modules connected by a backplane 32a. These modules include a CPU module 36, a calibration module 37 as well as a pulse generator module 38. The CPU module 36 connects to the operator console 12 through a data link 40. The Mill system control 32 receives commands from the operator through the data link 40 to indicate the scan sequence that is to be performed. The CPU module 36 operates the system components to carry out the desired scan sequence and produces data which indicates the timing, strength and shape of the RF pulses produced, and the timing and length of the data acquisition window. The CPU module 36 connects to components that are operated by the MRI controller 32, including the pulse generator module 38 which controls a gradient amplifier 42, a physiological acquisition controller (PAC) 44, and a scan room interface circuit 46.

In one example, the CPU module 36 receives patient data from the physiological acquisition controller 44, which receives signals from sensors connected to the object, such as ECG signals received from electrodes attached to the patient. As used herein, an object is a human (or patient), an animal, or a phantom. The CPU module 36 receives, via the scan room interface circuit 46, signals from the sensors associated with the condition of the patient and the magnet system. The scan room interface circuit 46 also enables the MRI controller 33 to command a patient positioning system 48 to move the patient to a desired position for scanning.

A whole-body RF coil 56 is used for transmitting the waveform towards subject anatomy. The whole body-RF coil 56 may be a body coil. An RF coil 57 may also be a local coil that may be placed in more proximity to the subject anatomy than a body coil 56. RF coil 57 may be used for receiving the signals from the subject anatomy. The RF coil 57 may also be a surface coil. Typical surface coil has multiple receiving elements. Using the combination of both a body coil 56 and a surface coil 57 is known to provide better image quality.

The pulse generator module 38 may operate the gradient amplifiers 42 to achieve desired timing and shape of the gradient pulses that are produced during the scan. The gradient waveforms produced by the pulse generator module 38 may be applied to the gradient amplifier system 42 having Gx, Gy, and Gz amplifiers. Each gradient amplifier excites a corresponding physical gradient coil in a gradient coil assembly 50, to produce the magnetic field gradients used for spatially encoding acquired signals. The gradient coil assembly 50 may form part of a magnet assembly 52, which also includes a polarizing magnet 54 (which, in operation, provides a longitudinal magnetic field $B_0$ throughout a target volume 55 that is enclosed by the magnet assembly 52 and a whole-body RF coil 56 (which, in operation, provides a transverse magnetic field B1 that is generally perpendicular to B0 throughout the target volume 55. A transceiver module 58 in the MRI system control 32 produces pulses that may be amplified by an RF amplifier 60 and coupled to the RF coil 56 by a transmit/receive switch 62. The resulting signals emitted by the excited nuclei in the subject anatomy may be sensed by receiving coils (not shown) and provided to a preamplifier 64 through the transmit/receive switch 62. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the receiving coil during the receive mode.

The MR signals produced from excitation of the target are digitized by the transceiver module 58. The MR system control 32 then processes the digitized signals by Fourier transform to produce k-space data, which is transferred to a memory module 66, or other computer readable media, via the MRI system control 32. "Computer readable media" may include, for example, structures configured so that electrical, optical, or magnetic states may be fixed in a manner perceptible and reproducible by a conventional computer (e.g., text or images printed to paper or displayed on a screen, optical discs, or other optical storage media, "flash" memory, EEPROM, SDRAM, or other electrical storage media; floppy or other magnetic discs, magnetic tape, or other magnetic storage media).

A scan is complete when an array of raw k-space data has been acquired in the computer readable media 66. This raw k-space data is rearranged into separate k-space data arrays for each image to be reconstructed, and each of these k-space data arrays is input to an array processor 68, which operates to reconstruct the data into an array of image data, using a reconstruction algorithm such as a Fourier transform. When the full k-space data is obtained, it represents entire volume of the subject body and the k-space so obtained may be referred as the reference k-space. Similarly, when only the partial k-space data is obtained, the image may be referred as the partial k-space. This image data is conveyed through the data link 34 to the computer system 20 and stored in memory. In response to the commands received from the operator console 12, this image data may be archived in a long-term storage or may be further processed by the image processor 22 and conveyed to the operator console 12 and presented on the display 16.

MR signals are represented by complex numbers, where each location at the k-space is represented by a complex number, with I and Q quadrature MR signals being the real and imaginary components. Complex MR images may be reconstructed based on I and Q quadrature MR signals, using processes such as Fourier transform of the k-space MR data. Complex MR images are MR images with each pixel represented by a complex number, which also has a real component and an imaginary component. The magnitude M of the received MR signal may be determined as the square root of the sum of the squares of the I and Q quadrature components of the received MR signal as in Eq. (3) below:

$$M = \sqrt{I^2 + Q^2} \quad (1)$$

and the phase $\phi$ of the received MR signal may also be determined as in eq. (2) below:

$$\phi = \tan^{-1}\left(\frac{Q}{I}\right) \quad (2)$$

As discussed earlier, a calibration scan is very important for the MRI system. The calibration scan acquires low resolution surface coil and body coil images also called as calibration images. A plurality of calibration parameters may be determined from these calibration images. In one embodiment, the calibration parameters may be maps derived from the calibration images. The calibration parameters are used for auto coil selection, channel compression, channel combination, parallel imaging and image intensity correction. Once the calibration parameters are determined, these parameters can be used later in combination with MR image data of the object acquired during the main scan to generate the image of the object.

In accordance with an embodiment of the invention, a calibration scan technique that employs a radial sampling scheme is presented to obtain a calibration k-space where endpoints of each calibration k-space line follow a spiral path in time. The technique employs a pulse sequence with low flip angle RF train and ultra-short Repetition Time (TR) and therefore, the calibration scan presented herein is very fast. Moreover, there is no MR signal dephasing because the MR signal is immediately acquired after each RF pulse with zero echo time (ZTE). The calibration scan presented herewith is also silent because a spiral view order is used to minimize the gradient change steps.

Figure 2:
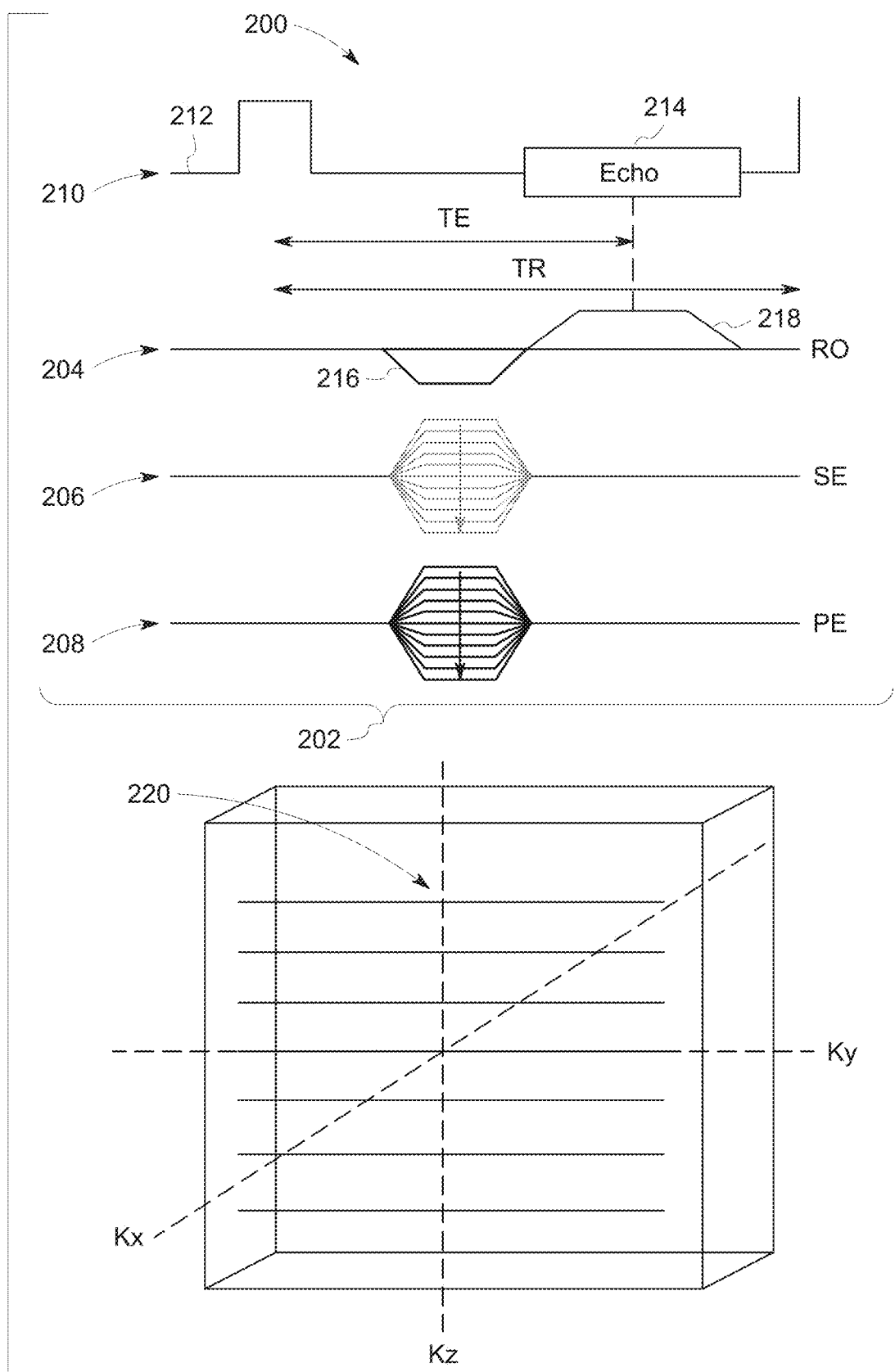
FIG. 2 is a schematic diagram of a regular 3-dimensional (3D) gradient echo pulse sequence diagram and a corresponding 3D cartesian k-space trajectory for a MRI system.

FIG. 2 is a schematic diagram of a regular 3-dimensional (3D) gradient echo pulse sequence diagram 202 and a corresponding k-space trajectory 200 for the MRI system. The k-space 200 shown is a regular 3D cartesian k-space. In general, k-space 200 represents data directly obtained from the MR signal wherein the k-space kx-ky-kz values correspond to spatial frequencies of the MR image in three dimensions. The pulse sequences diagram 202 may be generated by different modules of MRI system control 32 of FIG. 1.

Plot 204 shows a readout gradient waveform (RO), plot 208 shows a phase encoding gradient waveform (PE) and plot 206 shows a slice encoding gradient waveform (SE). The gradient waveforms 204, 206 and 208 are generated by the physical gradient coils in a gradient coil assembly 50. Further, plot 210 shows RF waveform which excites RF coil 56 and generates a gradient echo signal (or MR signal). The RF waveform 210 includes RF pulses 212 that are repeated at a time interval TR (Repetition time). With each repetition TR, a k-space line 220 of the k-space 200 is filled. The 3D k-space data is thus acquired in a layer-by-layer fashion.

The readout gradient waveform 204 has one upward lobe 218 called as the main or rephase readout gradient and one downward lobe 216 which is called as a readout dephasing lobe. The readout dephasing lobe 216 is followed by the rephasing lobe 219. As will be appreciated by those skilled in the art, the readout rephasing lobe 218 helps correct for the phase dispersion of transverse magnetization that occurs concomitant with application of the readout dephasing gradient 216. The time from the center of one RF pulse to the center of the echo signal 214 or the center of the rephase readout gradient 218 is called as echo time (TE). In one embodiment, the repetition time TR for the regular 3-dimensional (3D) gradient echo is in the range from about 1.7 milliseconds to about 4.6 milliseconds whereas the echo time TE is in the range from about 0.5 milliseconds to about 2.5 milliseconds.

The slice encoding gradient 206 is applied with a different amplitude (indicated by the horizontal hatchmarks/dash lines) for each repetition time TR of the pulse sequence to provide a different degree of slice encoding on each repetition. In general, the amplitude of first slice encoding gradient 206 determines which area of the k-space 200 gets filled. If the amplitude is positive then the upper half of the k-space 200 gets filled. On the other hand, if the amplitude of the first slice encoding gradient 208 is negative, the lower half of the k-space 200 gets filled.

The phase encoding gradient 208 is applied with a different amplitude (indicated by the horizontal hatchmarks/dash lines) for each repetition time TR of the pulse sequence to provide a different degree of phase encoding on each repetition. In general, the amplitude of first phase encoding gradient 208 determines which area of the k-space 200 gets filled. If the amplitude is positive then the right side area of the k-space 200 gets filled. On the other hand, if the amplitude of the first phase encoding gradient 208 is negative then the left side area of the k-space 200 gets filled. In one embodiment, the slice encoding gradient waveform 206 is first turned on to a fixed value (kz), and the in-plane phase-encode gradient 208 is stepped through its full range of possible values (from –ky to +ky). It should also be noted that the waveforms 206, 208 are applied simultaneously with the readout dephasing lobe 216.

It should be noted during each TR, the gradient waveforms 204, 206, 208 rise from an initial value (e.g., 0), ramp up and ramp down their magnitudes sharply, and return back to the initial value at the end of TR. Since the gradients signal is ramping up and ramping down during each TR, the MRI scan with this technique is very loud. Also as discussed earlier, although a calibration scan with the above cartesian technique is very fast, it causes significant signal dephasing in the calibration data at certain areas because the TE could be large, especially for quiet scans wherein the gradients have to be derated. Therefore, a calibration scan that employs a zero echo time (ZTE) radial sampling scheme where endpoints of each calibration k-space line follow a spiral path is proposed herewith.

Figure 3:
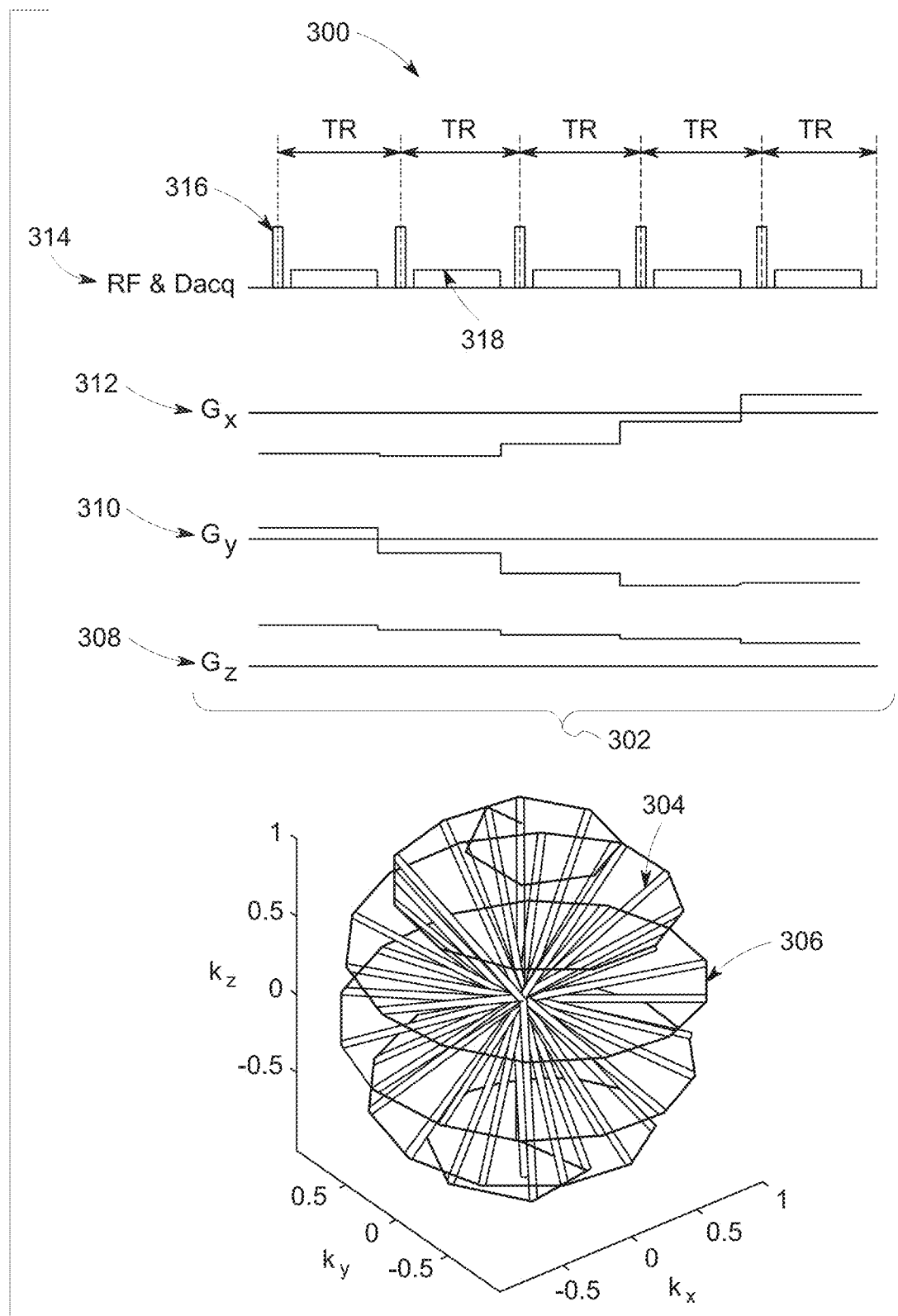
FIG. 3 is a schematic diagram of a spiral zero echo time (ZTE) radial sampling pulse sequence and corresponding k-space trajectory in accordance with an embodiment of the present technique.

FIG. 3 is a schematic diagram depicting a spiral ZTE radial sampling pulse sequence 302 and corresponding k-space trajectory 300 in accordance with an embodiment of the present technique. It should be noted that the k-space trajectory 300 is referred to herein as ZTE (or spiral ZTE) radial k-space trajectory and the related calibration technique is also referred to ZTE (or spiral ZTE) radial calibration technique. In the ZTE radial k-space trajectory 300, each k-space line 304 starts from the center of the k-space 300. Further, the endpoints of each radial k-space line 304 follow a spiral path 306 in time. In general, k-space 300 represents 3D data directly obtained from the MR signal.

The pulse sequences diagram 302 may be generated by different modules of MM system control 32 of FIG. 1. In the pulse sequence diagram 302, plot 312 shows a gradient waveform along axis x, plot 310 shows a gradient waveform along axis y and plot 308 shows a gradient waveform along axis z. Each gradient waveforms 312, 310 and 308 is generated by the gradient coil assembly.

Further, plot 314 shows RF waveform 316 which excites RF coil 56 and generates a corresponding MR signal 318. The RF waveform 316 includes RF pulses that are repeated at an ultra-short time interval TR compared to the repetition time TR in FIG. 2.

As against the technique in FIG. 2, in FIG. 3 technique, the gradient waveform Gx 312, Gy 310, and Gz 308 do not rise from an initial value and return to the same initial value during each TR. Rather these gradients increase or decrease in small amplitude steps from one TR to another TR. As can be seen from plot 312, the gradient Gx decreases slightly from first TR to second TR but then increases in small steps from second TR to third TR, third TR to fourth TR and fourth TR to fifth TR. Further, as can be seen from plot 310, the gradient Gy decreases in small steps from first TR to second TR, second TR to third TR, third TR to fourth TR but then increase in a small step from fourth TR to fifth TR. Moreover, as can be seen from plot 308, the gradient Gz decreases in small steps from first TR to second TR, second TR to third TR, third TR to fourth TR and fourth TR to fifth TR. It should be noted that the increase and decrease of gradients shown in FIG. 3 is only one example and in other embodiments, the gradient step changes may be different. Since the gradients are not changing sharply in amplitude, in this technique, the MR scan is generally silent and not loud.

In the spiral ZTE pulse sequence, the small step changes of readout gradient waveform (e.g., 312) are applied prior to the RF pulse 316. Thus, the MR signal is acquired right after the RF pulses and starts from the k-space center. Because, the changes of readout gradient waveform is applied prior to the RF pulse, the echo time TE is approximately zero. In one embodiment, the repetition time TR for the ZTE pulse sequence is about 0.6 milliseconds whereas the echo time TE is about 0 milliseconds. Another characteristic of the pulse sequence is that the flip angle which is the amount of rotation the net magnetization experiences is low such that the MR signal is not over saturated by the train of RF pulses. In one embodiment, the flip angle may range from 1 degree to 5 degrees.

With each repetition TR, a k-space line 304 (also called a radial spoke) of the k-space 300 is filled. Moreover, each k-space line 304 starts from the center of the k-space 300. The small change introduced by the small amplitude steps will ensure an adjacent k-space line be acquired in next TR. A series of the small changes across many TRs will ensure the endpoints of each k-space line 304 follow a spiral path 306 in time. In other words, the k-space 300 is sampled with radial spokes that start from the center of k-space 300 and follow a spiral path.

Figure 4:
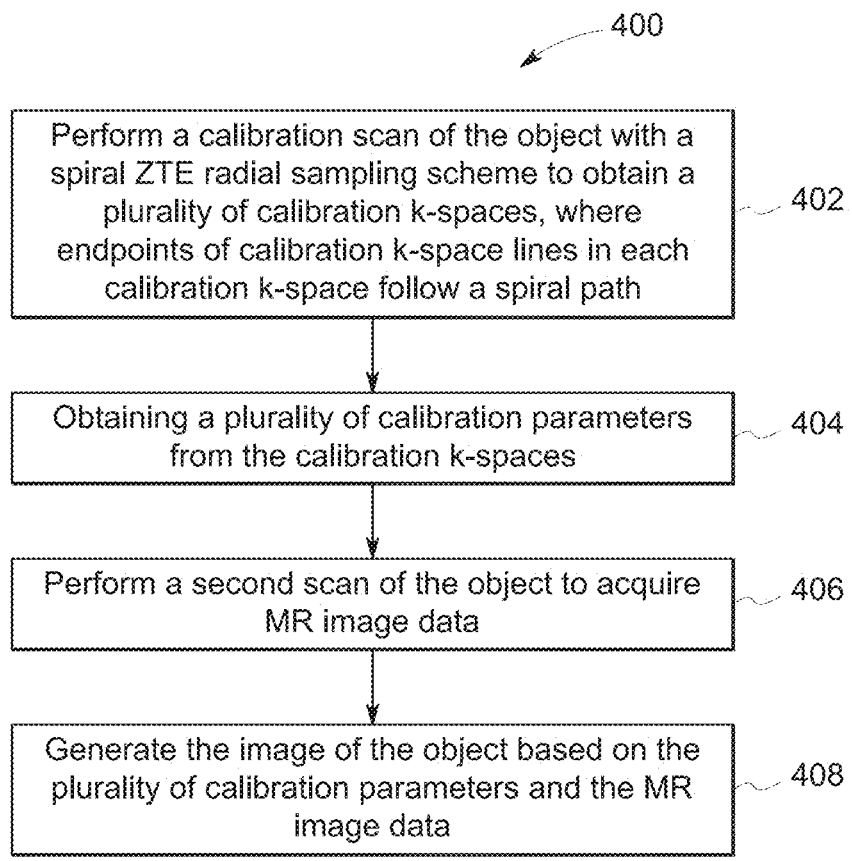
FIG. 4 is a flowchart of a method for generating MR image of an object with a MRI system, in accordance with an embodiment of the present technique.

FIG. 4 is a flowchart of a method 400 for generating the MR image of an object with the MRI system 10 according to an embodiment of the present technique. The method 400 may be implemented on the MRI controller 33 in coordination with other components of the MRI system. At step 402, the method includes performing a calibration scan of the object with the spiral ZTE radial sampling scheme 302 shown in FIG. 3 to obtain a plurality of calibration k-spaces. Each of the calibration k-space is similar to k-space 300 where the endpoints of k-space lines follow a spiral path in time. During the calibration scan the patient is present in the MRI system 10 and the scan conducted is a low resolution scan as compared to the main scan of the object. In one embodiment, a plurality of k-spaces is obtained for each element of the surface coil 57. Also, a k-space is obtained for body coil 56.

At step 404, a plurality of calibration parameters is determined from the calibration k-spaces obtained in step 402. The plurality of calibration parameters may include sensitivity map for each element of the surface coil 57 for coil selection, image combination and parallel imaging. The plurality of calibration parameters may also include shading correction parameters to correct the non-uniformity of the surface coils.

In one embodiment, there may be sixteen (16) elements (i.e. channels) of the surface coil on top and sixteen (16) elements of the surface coil on the bottom of the object i.e., total thirty two (32) surface coil elements 57. However, different number of coil elements are possible in other cases. In one embodiment, the calibration parameter includes sensitivity maps of these coil elements. These sensitivity maps can be used to combine the calibration images from coil elements to obtain a single combined image. The calibration images from coil elements are obtained based on a Fourier transform of the respective k-space of the coil elements obtained at step 402. The combination is done by providing the weight values for signals at different points of origin within the field of view. For example, a coil element may detect the strongest signal near the area where the coil element is located. Therefore, a higher weightage may be given for the points where the strongest signals were obtained, and lower weightage may be given for the points where the weakest signals were obtained. In one embodiment, the sensitivity map for a surface coil element may be obtained by dividing calibration image of a coil element with the calibration image obtained by the body coil. Again, the calibration body coil image is obtained based on the k-space of the body coil obtained at step 402. Alternatively, the sensitivity map for a surface coil element may be obtained by dividing a calibration image of a coil element with a combined image combined from all coil element images.

The sensitivity maps mentioned above is also used to select the surface coil elements for the main scan data acquisition of the object. In some embodiments, the user may not be interested in the whole area of the anatomy. For example, the user may be interested in only the prescribed volume. In such a case, only the surface coil elements related to that volume need to be selected. Thus, based on the calibration data, only a few relevant number of coil elements may be selected to acquire the data and to reduce the final patient image reconstruction time. In one embodiment, the coil elements are determined based on their sensitivity maps data for various areas of interest.

Further, another calibration parameter referred above is the shading correction map. In MRI, shading artifacts may be present in the combined image. These shading artifacts are caused by non-uniformity of the surface coil. In one embodiment, the shading correction map is obtained by dividing the body coil calibration image by the combine surface coil calibration image.

At step 406, the main scan or a second scan of the object is performed to acquire MR image data. In one embodiment, the MR image data may the main k-space of the object. The second scan of the object may be performed using known pulse sequence techniques such as gradient echo pulse sequence, spin echo pulse sequence, fast spin echo pulse sequence. Once the main k-space of the object is obtained, the final image of the object is generated at step 408 using a mathematical relationship between at least one of the calibration parameters obtained in step 404 and the main k-space obtained at step 406. In one embodiment, the mathematical relationship may be a matrix multiplication between the sensitivity map and the MR image data.

FIG. 5 is a schematic diagram 600 depicting a comparison of images obtained with the cartesian 3D calibration technique and the spiral ZTE radial sampling calibration technique presented herein. Specifically, images 602 and 604 are the coronal and axial views of the object respectively obtained with the cartesian 3D calibration technique. Further, images 606 and 608 are the coronal and axial views respectively obtained with the spiral ZTE radial calibration technique presented herein. It can be seen that the signal dephasing in images 602 and 604 shown by arrows 610 and 612 is fully removed in images 606 and 608 obtained with the spiral ZTE radial calibration technique as shown by arrows 614 and 616 at the same locations.

FIG. 6 is another schematic diagram 700 depicting a comparison of images obtained with the cartesian 3D calibration technique and the spiral ZTE radial sampling calibration technique presented herein. Specifically, image 702 is a fast spin echo (FSE) short tau inversion recovery (STIR) image obtained with the cartesian 3D calibration technique. Further, image 704 is also the FSE STIR image obtained with the spiral ZTE radial sampling calibration technique presented herein. The arrow 706 in image 702 indicates a local signal loss artifact that disappears in image 704 as shown by arrow 708 at the same location. It should be noted that the signal dephasing 610, 612 of FIG. 5 and local signal loss artifact 706 in FIG. 6 is caused by B0 field distortion and long echo time (TE) in calibration pulse sequence which is not present in the spiral ZTE radial sampling calibration technique.

One of the advantages of the proposed calibration technique is that it has zero echo time (ZTE) and thus, there is no signal dephasing induced by the main magnetic field distortion. Moreover, the proposed calibration technique is quiet as compared to other calibration techniques. The technique is also fast as the acquisition time here is of the same order as cartesian 3D calibration. Further, because the proposed technique is a radial acquisition technique, it is also insensitive to the patient motion.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for generating an image of an object with a magnetic resonance imaging (MRI) system, the method comprising:
    performing by the MRI system a calibration scan of the object with a spiral zero echo time (ZTE) radial sampling scheme to obtain a plurality of calibration k-spaces, where endpoints of calibration k-space lines in each calibration k-space follow a spiral path;
    obtaining by the MRI system a plurality of calibration parameters from the plurality of calibration k-spaces;
    performing by the MRI system a second scan of the object to acquire the MR image data;
    generating by the MRI system the image of the object based on the plurality of calibration parameters and the MR image data; and
    displaying the image of the object on a display;
    wherein gradient waveforms for the MRI system increase or decrease in small steps between one repetition time to another repetition time.

2. A magnetic resonance imaging (MRI) system, comprising:
    a magnet configured to generate a polarizing magnetic field about at least a portion of an object arranged in the MRI system;
    a gradient coil assembly including a readout gradient coil, a phase gradient coil, a slice selection gradient coil configured to apply at least one gradient field to the polarizing magnetic field;
    a radio frequency (RF) system configured to apply an RF field to the object and to receive magnetic resonance signals from the object;
    a processing system programmed to:
        perform a calibration scan of the object with a spiral zero echo time (ZTE) radial sampling scheme to obtain a plurality of calibration k-spaces where endpoints of calibration k-space lines in each calibration k-space follow a spiral path;
        obtain a plurality of calibration parameters from the plurality of calibration k-spaces;

perform a second scan of the object to acquire the MR image data;

generate the image of the object based on the plurality of calibration parameters and the MR image data;

display the image of the object on a display;

wherein gradient waveforms for the MRI system increase or decrease in small steps between one repetition time to another repetition time.

3. A magnetic resonance imaging (MRI) system, comprising:

a magnet configured to generate a polarizing magnetic field about at least a portion of an object arranged in the MRI system;

a gradient coil assembly including a readout gradient coil, a phase gradient coil, a slice selection gradient coil configured to apply at least one gradient field to the polarizing magnetic field;

a radio frequency (RF) system configured to apply an RF field to the object and to receive magnetic resonance signals from the object;

a processing system programmed to:

perform a calibration scan of the object with a spiral zero echo time (ZTE) radial sampling scheme to obtain a plurality of calibration k-spaces where endpoints of calibration k-space lines in each calibration k-space follow a spiral path;

obtain a plurality of calibration parameters from the plurality of calibration k-spaces;

perform a second scan of the object to acquire the MR image data;

generate the image of the object based on the plurality of calibration parameters and the MR image data;

display the image of the object on a display; and wherein gradient waveforms for the spiral ZTE radial sampling scheme are not ramped up or ramped down between one repetition time.

4. The method of claim 1, wherein gradient waveforms for the spiral ZTE radial sampling scheme are not ramped up or ramped down between one repetition time.

5. The method of claim 1, wherein amplitudes of the small step are determined such that the endpoints of calibration k-space lines follow a spiral path.

6. The method of claim 1, wherein the second scan of the object is performed with a gradient echo pulse sequence technique, a spin echo pulse sequence technique or a fast spin echo pulse sequence technique.

7. The method of claim 1, wherein the plurality of calibration k-spaces include calibration k-spaces for a plurality of surface coil elements and a body coil of the MRI system.

8. The MRI system of claim 2, wherein the second scan of the object is performed with a gradient echo pulse sequence technique, a radial pulse sequence technique or a spiral pulse sequence technique.

9. The MRI system of claim 2, wherein the plurality of calibration parameters includes sensitivity maps for a plurality of surface coil elements of the MRI system, and shading correction parameter to correct the non-uniformity of the surface coil elements.

10. The MRI system of claim 9, wherein generating the image of the object comprises using a matrix multiplication relationship between sensitivity maps and the MR image data.

11. The MRI system of claim 9, wherein the sensitivity maps are obtained by dividing at least one surface coil element image of the plurality of surface coil elements by a combined image obtained from the plurality of surface coil elements or a body coil image.

12. The method of claim 7, wherein the plurality of calibration parameters includes sensitivity maps of surface coil elements, and shading correction parameter to correct the non-uniformity of the surface coil elements.

13. The method of claim 7, wherein the sensitivity maps are used for selecting at least one surface coil element among the plurality of surface coil elements for the second scan of the object.

14. The MRI system of claim 9, wherein the shading correction parameter includes a compensation parameter that is obtained by dividing a body coil image with a combined image obtained from the plurality of surface coil elements.

15. The MRI system of claim 10, wherein the sensitivity maps provide weight values for MR signals at different points of origin within a field of view of the MRI system.

16. The method of claim 12, wherein generating the image of the object comprises using a matrix multiplication relationship between sensitivity maps and the MR image data.

17. The method of claim 12, wherein the sensitivity maps are obtained by dividing at least one surface coil element image of the plurality of surface coil elements by a combined image obtained from the plurality of surface coil elements or a body coil image.

18. The method of claim 12, wherein the sensitivity maps include weight values for MR signals at different points of origin within a field of view of the MRI system.

19. The method of claim 12, wherein the shading correction parameter includes a shading correction map that is obtained by dividing a body coil image with a combined image obtained from the plurality of surface coil elements.

* * * * *